(12) United States Patent
Gershfang et al.

(10) Patent No.: US 10,964,418 B2
(45) Date of Patent: *Mar. 30, 2021

(54) TECHNOLOGY FOR PROCESSING PRESCRIPTION MEDICATIONS FOR PICKUP BY INDIVIDUALS

(71) Applicant: WALGREEN CO., Deerfield, IL (US)

(72) Inventors: Igor Gershfang, Chicago, IL (US); Nimesh S. Jhaveri, Kildeer, IL (US); Mohsin Ovais Ansari, Highland Park, IL (US); Fauzia Somani, Glencoe, IL (US); Adam Robert Snopek, Chicago, IL (US)

(73) Assignee: WALGREEN CO., Deerfield, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/216,499

(22) Filed: Dec. 11, 2018

(65) Prior Publication Data

US 2019/0108900 A1 Apr. 11, 2019

Related U.S. Application Data

(63) Continuation of application No. 16/002,027, filed on Jun. 7, 2018.
(Continued)

(51) Int. Cl.
*G16H 20/10* (2018.01)
*G16H 20/13* (2018.01)
(Continued)

(52) U.S. Cl.
CPC ........... *G16H 20/10* (2018.01); *G06K 7/1413* (2013.01); *G06K 7/1417* (2013.01); *G16H 20/13* (2018.01); *G16H 80/00* (2018.01); *G16H 40/67* (2018.01)

(58) Field of Classification Search
CPC ........ G16H 20/10; G16H 20/13; G16H 80/00; G16H 40/67; G06K 7/1413; G06K 7/1417
(Continued)

(56) References Cited

U.S. PATENT DOCUMENTS 9,436,803 B2 9/2016 Rosenblum
9,679,114 B2 6/2017 Iantorno et al.
(Continued)

FOREIGN PATENT DOCUMENTS

WO WO-2011/153627 A2 12/2011
WO WO-2014/197855 A1 12/2014
(Continued)

OTHER PUBLICATIONS

Anonymous, QR Code Prescription and Supplement Tracker, Mar. 10, 2015, IP.com Prior Art Database Technical Disclosure, pp. 1-3 (Year: 2015).*
(Continued)

*Primary Examiner* — Joy Chng
(74) *Attorney, Agent, or Firm* — Marshall, Gerstein & Borun LLP; Randall G. Rueth

(57) ABSTRACT

Systems and methods may be provided that may enable an individual to retrieve one or more prescription products (e.g., product refills) from a self-service retrieval location such as a counter, drive-thru, drop box, or kiosk. A unique-machine readable code may be associated with a particular one or more prescription products (e.g., associated with a medical prescription of a patient). The unique machine-readable code may be provided to a computing device of the individual, along with an anticipated time of preparedness of the one or more products for retrieval at the retrieval location. Identification of the unique machine-readable code
(Continued)

may result in dispensing of the one or more prescription products associated at the retrieval location.

14 Claims, 9 Drawing Sheets

Related U.S. Application Data

(60) Provisional application No. 62/521,349, filed on Jun. 16, 2017.

(51) Int. Cl.
  *G16H 80/00* (2018.01)
  *G06K 7/14* (2006.01)
  *G16H 40/67* (2018.01)

(58) Field of Classification Search
  USPC .......................................................... 705/2–3
  See application file for complete search history.

(56) References Cited

U.S. PATENT DOCUMENTS

| | | |
|---|---|---|
| 2001/0042024 A1 | 11/2001 | Rogers |
| 2002/0111914 A1 | 8/2002 | Terada et al. |
| 2003/0050731 A1 | 3/2003 | Rosenblum |
| 2004/0107117 A1 | 6/2004 | Denny |
| 2005/0049746 A1 | 3/2005 | Rosenblum |
| 2009/0179735 A1 | 7/2009 | Van Rysselberghe |
| 2011/0307265 A1 | 12/2011 | Bannis |
| 2013/0339048 A1* | 12/2013 | Roberts .............. G06F 19/3456 705/2 |
| 2014/0361076 A1* | 12/2014 | Iantorno ................ G06F 19/30 235/381 |
| 2015/0106296 A1 | 4/2015 | Robinson et al. |
| 2015/0317860 A1 | 11/2015 | Hubner et al. |
| 2015/0356664 A1 | 12/2015 | Mackler |
| 2016/0140487 A1 | 5/2016 | Tibbs et al. |
| 2017/0083685 A1 | 3/2017 | Rosenblum |

FOREIGN PATENT DOCUMENTS

| | | | |
|---|---|---|---|
| WO | WO-2015/048496 A1 | 4/2015 | |
| WO | WO-2015048496 A1 * | 4/2015 | ......... G06Q 10/0836 |

OTHER PUBLICATIONS

European Patent Application No. 18177277.3, Extended European Search Report, dated Nov. 22, 2018.
European Patent Application No. 18177272.4, Extended European Search Report, dated Nov. 22, 2018.
European Patent Application No. 18177264.1, Extended European Search Report, dated Nov. 22, 2018.
European Patent Application No. 18177264.1, Extended European Search Report, dated Nov. 20, 2018.
Non-Final Office Action, U.S. Appl. No. 16/216,499, dated Mar. 7, 2019.
Final Office Action, U.S. Appl. No. 16/216,499, dated Sep. 19, 2019.
Non-Final Office Action, U.S. Appl. No. 16/216,499, dated Feb. 6, 2020.
Non-Final Office Action, U.S. Appl. No. 16/216,499, dated Jul. 10, 2020.
Non-Final Office Action, U.S. Appl. No. 16/216,534, dated Feb. 15, 2019.
Final Office Action, U.S. Appl. No. 16/216,534, dated Jun. 19, 2019.
Non-Final Office Action, U.S. Appl. No. 16/216,534, dated Apr. 15, 2020.
Wikipedia, QR Code, Dec. 2015 (Year: 2015).
Non-Final Office Action, U.S. Appl. No. 16/002,115, dated Jun. 2, 2020.
Non-Final Office Action, U.S. Appl. No. 16/002,170, dated Feb. 21, 2020.

* cited by examiner

TECHNOLOGY FOR PROCESSING PRESCRIPTION MEDICATIONS FOR PICKUP BY INDIVIDUALS

RELATED APPLICATIONS

This application is a continuation application of U.S. patent application Ser. No. 16/002,027, which was filed Jun. 7, 2018, and entitled "Technology for Processing Prescription Medications for Pickup by Individuals," and which claims priority to and the benefit of the filing date of U.S. Provisional Application Ser. No. 62/521,349, which was filed Jun. 16, 2017, and entitled "Technology for Processing Prescription Medications for Pickup by Individuals." The present application claims priority from each of the above-referenced applications, and the disclosures of each of the above-referenced applications are hereby expressly incorporated herein by reference.

FIELD OF THE DISCLOSURE

This application relates generally relates to self-service prescription processing, and more particularly, to technology that may enable an individual to present a unique machine-readable code to obtain prescription products from a self-service location.

BACKGROUND

Generally, an individual (e.g., a patient, or a parent or caregiver of the patient), receiving a medical prescription or a refill thereof for a prescription product (e.g., a medication or a medical device) may be required to complete a multitude of tasks prior to receipt of the prescription product. For example, acquiring the prescription product may require the patient to verify the patient's identity or other personal information, consult a physician and or pharmacist, pay for the prescription product, manually drop off a prescription refill order at a pharmacy counter, retrieve the prescription refill at the pharmacy counter at a later time, acknowledge receipt, and/or other tasks. In practice, these tasks may place a significant burden on the patient and cause undue or even dangerous delay in receipt of the prescription product.

SUMMARY

A mobile and/or native desktop application for prescription processing may be provided to a patient and/or to a representative of the patient. The application may generally enable the patient or representative to independently complete vital prescription processing tasks. Upon completion, the application may issue a unique machine-readable code (a "prescription pass") associated with a medical prescription, that the patient or representative may present at a retrieval location to receive one or more prescription products associated with the medical prescription.

In one embodiment, a computer implemented method may be provided for identifying one or more products according to a unique machine-readable code. The method may include (1) generating, via one or more processors, a unique machine-readable code associated with one or more prescription products to be provided to an individual at a point of retrieval; (2) providing, via the one or more processors and via an application executing at a computing device associated with the individual, (i) the unique machine-readable code, and (ii) an anticipated time of preparedness of the one or more prescription products for retrieval at the point of retrieval; (3) detecting, via the one or more processors and via a scanning device at the point of retrieval, a scan of the unique machine-readable code; and/or (4) identifying, via the one or more processors, based upon the detected scan of the unique machine-readable code, the one or more prescription products to be provided at the point of retrieval. The method may include additional, fewer, or alternate actions, included those described herein.

In another embodiment, a computing system may be provided. The computing system may include (1) one or more processors, and (2) one or more memories storing non-transitory computer-executable instructions that, when executed via the one or more processors, cause the computing system to: (i) generate a unique machine-readable code associated with one or more prescription products to be provided to an individual at a point of retrieval, (ii) provide, via an application executing at a computing device associated with the individual, (a) the unique machine-readable code, and (b) an anticipated time of preparedness of the one or more prescription products for retrieval at the point of retrieval, (iii) detect, via a scanning device at a point of retrieval of the one or more prescription products, a scan of the unique machine-readable code, and/or (iv) identify, based upon the detected scan of the unique machine-readable code, the one or more prescription products to be provided at the point of retrieval. The system may include additional, fewer, or alternate components and/or actions, including those described herein.

In yet another embodiment, one or more computer-readable media may be provided. The one or more computer-readable media may store non-transitory executable instructions that, when executed via one or more processors, cause the one or more processors to: (1) generate a unique machine-readable code associated with one or more prescription products to be provided to an individual at a point of retrieval, (2) provide, via an application executing at a computing device associated with the individual, (i) the unique machine-readable code, and (ii) an anticipated time of preparedness of the one or more prescription products for retrieval at the point of retrieval, (3) detect, via a scanning device at a point of retrieval of the one or more prescription products, a scan of the unique machine-readable code, and/or (4) identify, based upon the detected scan of the unique machine-readable code, the one or more prescription products to be provided at the point of retrieval. The one or more computer-readable media may include additional, fewer, or alternate instructions, including those described herein.

DETAILED DESCRIPTION

Figure 1:
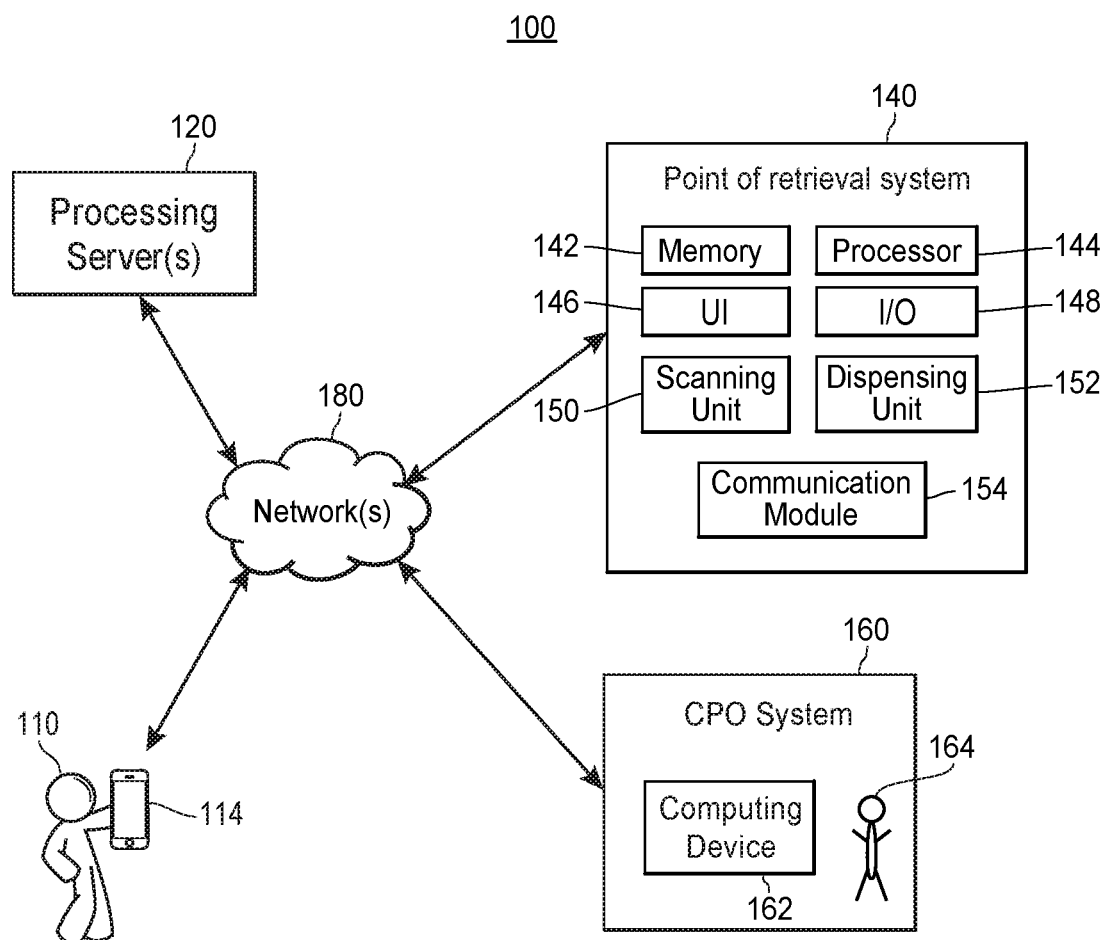
FIG. 1 depicts an overview of components and entities associated with the systems and methods described herein, in accordance with some embodiments.

The present embodiments may relate, inter alia, to technology (e.g., a mobile, desktop, or web application) to enable a user (e.g., a medical patient, or a parent or caregiver thereof) to retrieve (i.e., "pick up") one or more prescription products. According to certain aspects, a user may utilize the application to identify a new prescription or prescription refill and a location at which the user will retrieve the corresponding one or more prescription products. Identifying the pharmacy location may include identifying a particular point of retrieval (e.g., a pharmacy counter, kiosk, or drop box) within a venue (e.g., a pharmacy or a hospital) from which the user will retrieve the prescription product.

The user may further utilize the technology described herein to perform one or more tasks that may be necessary to retrieve the prescription product. For example, in some embodiments, the user may utilize the technology to provide identification, provide payment, designate one or more notifications for retrieval, and/or consult a remotely-located pharmacist by text, audio, and/or video communication session.

In any case, upon completion of any necessary steps, the technology described herein may provide the user with a "prescription pass" (e.g., a barcode, QR code, audio signal stored on an electronic device, etc.) that is redeemable to retrieve one or more prescription products. The user may bring the prescription pass to the point of retrieval, where scanning the prescription pass may identify the user, prescription, and/or prescription product(s) to be retrieved. Upon retrieval of the one or more prescription products, the user may complete any additional steps (e.g., receipt acknowledgement, agreement of a privacy notice, payment, etc.) that may be required to complete the prescription retrieval process.

In some embodiments, as will be described herein, the technology may provide additional features. For example, the technology may enable a user to provide payment for the one or more prescription products, and/or utilize an audio-video feature to connect to a remotely-located pharmacist to receive counseling related to the medical prescription and/or the one or more prescription products.

In some embodiments, the prescription pass may be transferable. A patient, for example, may transfer a prescription pass to an electronic device of another person such as a parent, guardian, or caregiver, such that the other person may retrieve the one or more prescription products.

The technology described herein may generally be implemented via a computer-implemented application, and the application may be configured to run on a mobile device (e.g., a smartphone), a laptop computer, a tablet, a desktop computer, etc. Accordingly, the functions of the technology may, for ease of description, often be described herein as being performed via an application, in particular a mobile smartphone application. It should be appreciated, however, that other implementations (e.g., via a web browser, via SMS text communication, etc.) may be possible.

The technology described herein therefore offers numerous benefits. In particular, systems and methods described herein may facilitate prescription/refill retrieval by connecting conventionally disparate steps of the prescription refill retrieval process through a unified application. Further, the application, and in particular the prescription pass, may enable self-service functionality for a user seeking a new prescription or a prescription refill. Additionally, use of the prescription technology may enable significantly faster prescription processing and retrieval, compared to conventional methods.

Thus, the technology described in this application addresses challenges that are unique to prescription issuance and management. Conventionally, a patient retrieving a prescription may be required to perform disparate tasks in order to obtain a prescription product. The technology described herein offers the benefits of increasing the timeliness of prescription delivery, bettering the ability of a user to track prescription products, and potentially increasing user confidence in the prescription experience.

As used herein, a "user" also referred to herein as an "individual," may refer to a person who uses the technology described herein to facilitate the retrieval of the prescription product. Accordingly, the user may be the patient for whom the prescription was issued. Alternatively, the user may be a parent, a guardian, or otherwise a caregiver for the person for whom the prescription was issued, and the user may utilize the technology to retrieve the prescription product on behalf of the patient for whom the prescription was issued.

As used herein, a "prescription" may refer to an instruction (e.g., a written instruction) given by a physician, authorizing a patient to be provided one or more prescription products (e.g., a medication or a medical device). However, in some instances, a "prescription" may refer to the prescription product itself. A prescription may include a "prescription refill" which, as used herein, may refer to an instruction or authorization for the patient to be provided a partial or complete refill or replacement of at least one of the one or more prescription products, and additionally or alternatively may refer to the refilled or replaced one or more prescription products themselves. While prescription refills are sometimes described herein, it should be understood that the technology described herein may additionally or alternatively be used for retrieval of a newly prescription product. Furthermore, it is particularly noted that instances of "a prescription product" described herein, one or more than one prescription products may be envisioned, unless specifically indicated otherwise.

FIG. 1 illustrates an overview of a system 100 of components configured to facilitate the systems and methods described herein. It should be appreciated that the system 100 is merely an example system. Other systems, including those with additional, fewer, or different components, may be possible in some embodiments.

As illustrated in FIG. 1, the system 100 may include a user 110 having or interacting with an electronic device 114. The user 110 may be, for example, an individual to whom a medical prescription is prescribed (also referred to herein as a "patient"), or a parent, guardian, or other caregiver who is authorized to provide care (e.g., request and retrieve prescription products) on behalf of the patient. In any case, the user 110 may generally utilize the electronic device 114 to perform actions described herein to facilitate issuance of a prescription pass and redemption of the prescription pass at a point of retrieval system 140. The actions described herein may be performed via an application running on the electronic device 114, for example.

The electronic device 114 may be for example, a smartphone, a tablet, a laptop computer, a desktop computer, a smart wearable device, or another suitable computing device. While one electronic device 114 is depicted in FIG. 1, it should be appreciated that, in some embodiments, the user may utilize a combination of two or more electronic devices 114 to perform actions described herein. Components of the electronic device 114 will be discussed in further detail with regard to FIG. 2.

The electronic device 114 may be configured to communicate with other components of the system 100 over one or more networks 180. In embodiments, the network(s) 180 may support any suitable type of data communication via any suitable standard or technology (e.g., GSM, CDMA, TDMA, WCDMA, LTE, EDGE, OFDM, GPRS, EV-DO, UWB, Internet, IEEE 802 including Ethernet, WiMAX, Wi-Fi, Bluetooth and others). Accordingly, the network(s) 180 may include one or more wired connections, one or more wireless connections, or some combination thereof. The network(s) 180 may include one or more public networks, one or more private networks, or some combination thereof.

The system 100 may further include one or more backend processing servers 120. Generally, the processing server(s) 120 may be configured to communicate with other components of the system 100 over the network(s) 180, to implement backend functionality of an application for issuing and/or redeeming a prescription pass, for example. Components of the processing server(s) 120 will be discussed in further detail with regard to FIG. 2.

The system 100 may further include a point of retrieval system 140. Generally, as described herein, a point of retrieval system 140 may be disposed at a location (a "point of retrieval," such as a pharmacy counter, drop box, or kiosk) within a venue (e.g., a hospital or pharmacy), at which one or more prescription products may be retrieved. The point of retrieval system 140 may generally be configured to dispense one or more prescription products upon scanning and identification of the prescription pass' unique machine readable code associated with the prescription and one or more prescription products, as will be described further herein.

It should be understood that, in some embodiments, the point of retrieval system 140 (i.e., the components thereof to be described herein) may be disposed at a multiplicity of locations (e.g., a chain of pharmacies, multiple pharmacy counters, kiosks, and/or drop boxes within a particular pharmacy, etc.). Accordingly, though retrieval of prescription products at one particular point of retrieval (and hence, one point of retrieval system 140) may be discussed herein, it should be understood that many point of retrieval systems 140 may be possible, in some embodiments, with each point of retrieval system 140 corresponding to a possible point of retrieval for prescription products. In such embodiments, the point of retrieval system 140 may communicate over the network(s) 180.

The point of retrieval system 140 may include one or more memories 142 (e.g., RAM, ROM, EPROM, EEPROM, removable memory, etc.), one or more processors 144. The memory 142 may store an operating system capable of facilitating the functionalities of point of retrieval system 140 described herein, as well as one or more applications (i.e., machine readable instructions). The memory 142 may further store information pertaining to patients, representatives of patients, medical prescriptions, prescription products stored at the point of retrieval, payment management, receipt acknowledgement, etc.

The point of retrieval system 140 may include one or more user interfaces 146 which may display and/or receive (via a screen, audio, etc.) prompts or other information to a user via one or more input/output (I/O) units 148 (e.g., a touchscreen, audio unit, keypad, etc.). Generally, the user interface(s) 146 and the I/O unit(s) 148 may be utilized to perform any tasks that may be necessary before, at the time of, or after dispensing of prescription products.

The point of retrieval system 140 may include one or more scanning units 150. The one or more scanning units 150 may include, for example, a barcode reader, a two-dimensional matrix barcode (e.g., QR code) reader, an alphanumeric code reader, an audio receiver, and/or another suitable technology capable of detecting and identifying a unique machine-readable code associated with a medical prescription for one or more prescription products.

In some embodiments, the point of retrieval system 140 may include one or more automatic dispensing units 152 configured to dispense one or more prescription products upon identification of the medical prescription and/or the prescription product(s) with which the prescription is associated. In some embodiments, the automatic dispensing unit 152 may be omitted, and at least some of the tasks thereof may be performed by a human operator (e.g., a patient or pharmacist) of the point of retrieval system 140.

The point of retrieval system 140 may further include one or more communication modules 155. In some embodiments, the communication module(s) 155 may include one or more transceivers (e.g., WWAN, WLAN, and/or WPAN transceivers, etc.) functioning in accordance with IEEE standards, 3GPP standards, or other standards. Generally, the communication module(s) 128 may be configured to send and/or receive data to facilitate actions of the point of retrieval system 140 described herein. The point of retrieval system 140 may, for example, communicate with the server(s) 120 to send, retrieve, and/or verify information associated with an individual retrieving prescription products, identify a unique machine-readable code associated with a medical prescription, receive payment, etc. In some embodiments, the functions of the communication module(s) 154 may be integrated in the processor(s) 144.

The system 100 may further include a central pharmacy operations (CPO) system 160. Generally, the CPO system 160 may provide services to retrieval locations and individuals, including enabling an individual (e.g., a patient or an individual retrieving prescription product(s) on behalf of the patient to consult a remotely located pharmacist or other professional prior to, during, or after retrieval of the prescription product(s). Accordingly, the CPO system 160 may include one or more computing devices 162 operated by one or more remotely located pharmacists or physicians 164 to communicate with a user 110 of the electronic device 114 via the network(s) 180. Functions and actions of the CPO system 160 will be described in further detail herein.

Figure 2:
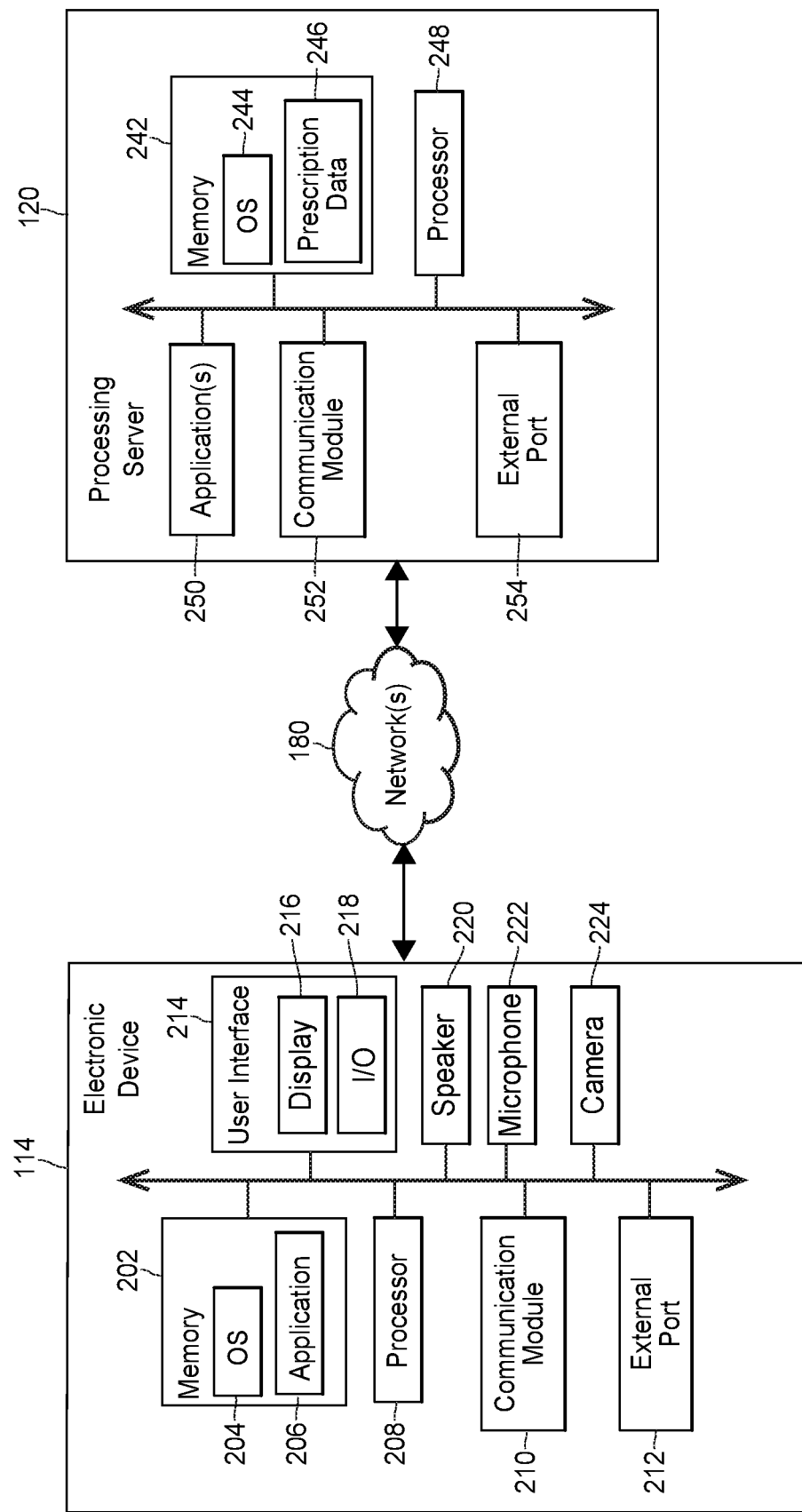
FIG. 2 depicts an enhanced view of a computing device depicted previously in FIG. 1, in accordance with some embodiments.

FIG. 2 depicts a detailed view of an electronic device 114 and a processing server 120 communicating via the network(s) 180. The electronic device 114 may be a device owned and/or used by the individual 110 to perform the actions described herein. The electronic device 114 may be, for example, a mobile phone (e.g., smartphone), a tablet, a laptop computer, a desktop computer, a smart wearable device, or another suitable electronic device. Multiple electronic devices 114 may be possible, and may include a combination of the devices listed above. Further, additional, fewer, or alternate components of the electronic device 114 may be possible, in some embodiments.

In any case, the electronic device 114 may include one or more memories 202 (e.g., RAM, ROM, EPROM, EEPROM, removable memory, etc.). The one or more memories 202 may include an operating system 204 capable of facilitating the functions of the electronic device 114 described herein. The one or more memories 202 may further include one or more applications 206, one or more of which may be executed via one or more processors 208 to perform the functions described herein (e.g., a "prescription pass application"). The electronic device 114 may further include one or more communication modules 210. In some embodiments, the communication module(s) 128 may include one or more transceivers (e.g., WWAN, WLAN, and/or WPAN transceivers, etc.) functioning in accordance with IEEE standards, 3GPP standards, or other standards. Generally, the communication module(s) 210 may be configured to communicate via a communicative connection to the network(s) 180 via one or more external ports 212, to communicate with the processing server(s) 120, the point of retrieval system 140, and/or the CPO system 160, as described herein. In some embodiments, the communication module(s) 210 may be integrated in the one or more processors 208.

The electronic device 114 may further include one or more user interfaces 214, which may be configured to enable the user 110 to use the electronic device 114 to perform the actions described herein. The user interface(s) 214 may include a display screen 216, via which the user 110 may, for example, view medical prescriptions, prescription products, and/or issued prescription passes (e.g., view a QR code to be scanned at a point of retrieval). The user interface(s) 214 may further include one or more input/output (I/O) units 218 (e.g., a touchscreen, keypad, stylus, mouse, etc.), which may enable user participation in a prescription pass application described herein, for example.

In some embodiments, the electronic device may further include one or more speakers 220 and/or one or more microphones 222, which may enable the electronic device 114 to provide audio output and/or receive audio input, respectively, to enable at least some aspects of the technology described herein. For example, in some embodiments, the speaker 220 may provide one or more prompts (e.g., a prompt to select a medical prescription, or to provide identifying information such as a phone number) to the user 110, and the microphone 222 may, for example, receive one or more user selections of the prompts and/or other application navigation instructions. Additionally or alternatively, the user 110 may utilize the speaker 220, the microphone 222, and/or a camera 224 to conduct an audio/video consultation session with a remotely-located physician or pharmacist, enabling the user 110 to receive counseling regarding a prescription or product before, during, or after product retrieval, for example.

The one or more processing server(s) 120 may include one or more memories 242 (e.g., RAM, ROM, EPROM, EEPROM, removable memory, etc.) as well as one or more processors 248. The one or more memories 242 may store an operating system 244 that may be executed via the one or more processors 248 to execute the functions of the processing server(s) 120 described herein, via one or more applications 250, for example. The one or more memories 246 may further store prescription data 246 (e.g., data pertaining to patients, prescription passes, medical prescriptions, products, and the like. Accordingly, the processing server(s) 120 may be associated with, for example, a hospital, a pharmacy, or some combination thereof.

The processing server(s) 120 may additionally include one or more communication modules 252 configured to communicate data via the one or more networks 180. In some embodiments, the communication module(s) 252 may include one or more transceivers (e.g., WWAN, WLAN, and/or WPAN transceivers, etc.) functioning in accordance with IEEE standards, 3GPP standards, or other standards. Generally, the communication module(s) 252 may be configured to send and/or data via one or more external ports 254 to facilitate actions of the server(s) 120 described herein. In some embodiments, the functions of the communication module(s) 252 may be integrated in the processor(s) 248.

In some embodiments, one or more processing servers 120 may be disposed at a point of retrieval of prescription products, and accordingly may include some or all of the components of the point of retrieval system 140. For example, one or more processing servers may include one or more user interfaces 146, one or more I/O units 148, one or more scanning units 150, and/or one or more dispensing units 152 configured to perform actions described herein with regard to the point of retrieval system 140.

Acquiring a Prescription Pass Application

Figure 3:
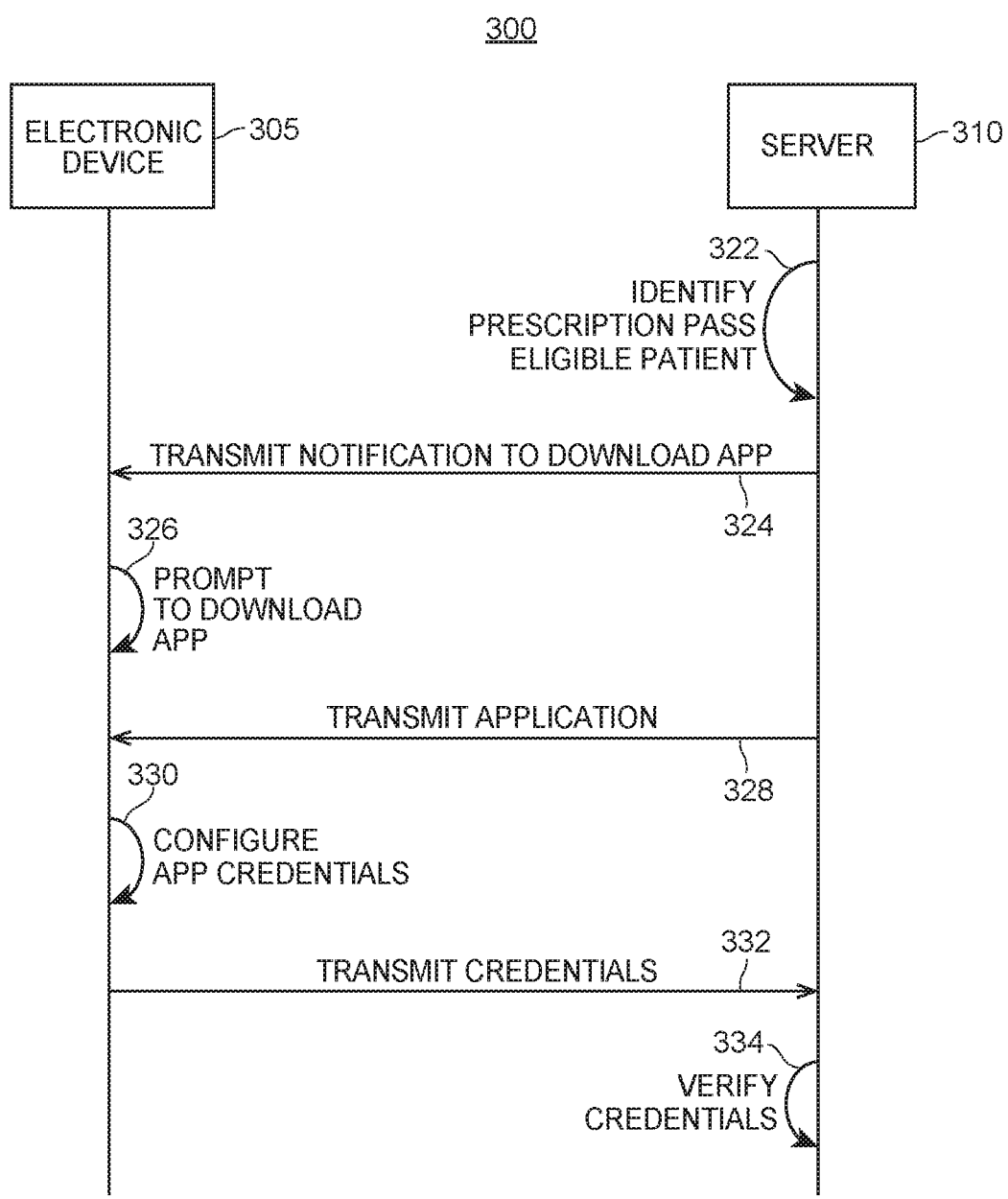
FIG. 3 depicts an example signal diagram associated with acquiring a prescription pass application.

FIG. 3 depicts a signal diagram 300 associated with acquiring a prescription pass application at an electronic device, in accordance with some embodiments. The signal diagram 300 includes an electronic device 305 (such as the electronic device 114 as discussed with respect to FIGS. 1 and 2) operated by a user. In some embodiments, the user may be a patient associated with one or more medical prescriptions. Additionally or alternatively, a user of the electronic device 305 may include a representative (e.g., a parent, guardian, or another caregiver) authorized to request and/or receive prescription products and/or refills on behalf of a patient. It should be appreciated that actions attributed to the electronic device 305 in FIG. 3 may include actions performed on the electronic device 305 by a user of the electronic device 305 (e.g., a button press, data entry, etc.).

The signal diagram 300 further includes a server 310 (such as the processing server 120 as discussed with respect to FIG. 1). It should be particularly noted that, while one server 310 is described for ease of description, one or more servers 310 may be possible.

Further, it should be appreciated that, while a downloadable prescription pass application is described herein, other implementations are possible. For example, in some embodiments, a user of the electronic device 305 may additionally or alternatively utilize a web browser on an electronic device to request and receive prescription products as described in this detailed description. Additionally, it should be appreciated that additional, fewer, or alternative components, devices, or actions may be envisioned, in some embodiments.

The signal diagram 300 may begin when the server identifies (322) a patient who is eligible to receive prescription products via the prescription pass technology described herein. An eligible patient may be, for example, a patient with one or more past, current, or future medical prescriptions associated with one or more prescription products (e.g., a mediation or medical device) eligible to be received via the technologies.

After identifying an eligible patient, the server 310 may transmit or otherwise cause transmission (324), to the electronic device 305, of a notification to download a prescription pass application. The prescription pass application may be, for example, a mobile device application (e.g., smartphone application) compatible with a mobile electronic device (e.g., a smartphone), enabling a user of the electronic device 305 to request and receive prescription products as described herein. The notification to download the application may include, in some embodiments, a phone call, an SMS text message, a push notification, an email, and/or another suitable means. In any case, after receiving the notification, the user may prompt (326) installation of the prescription pass application on the electronic device 305. The prompt may include, for example, a voice command, a screen touch, a mouse click, and/or another suitable interaction from the user.

Once the user has download the application to the electronic device 305, the user may further configure (328) the application, for example, with credentials pertaining to the patient and/or the representative of the patient. In some embodiments, for example, configuring the prescription pass application may include providing proof of identity, agreeing to a privacy notice, identifying a home location, and/or configuring current medical prescriptions in the application. In some embodiments, the electronic device 305 may transmit the credentials (330) to the server, and the server may verify the credentials (332).

Issuing a Prescription Pass

Figure 4:
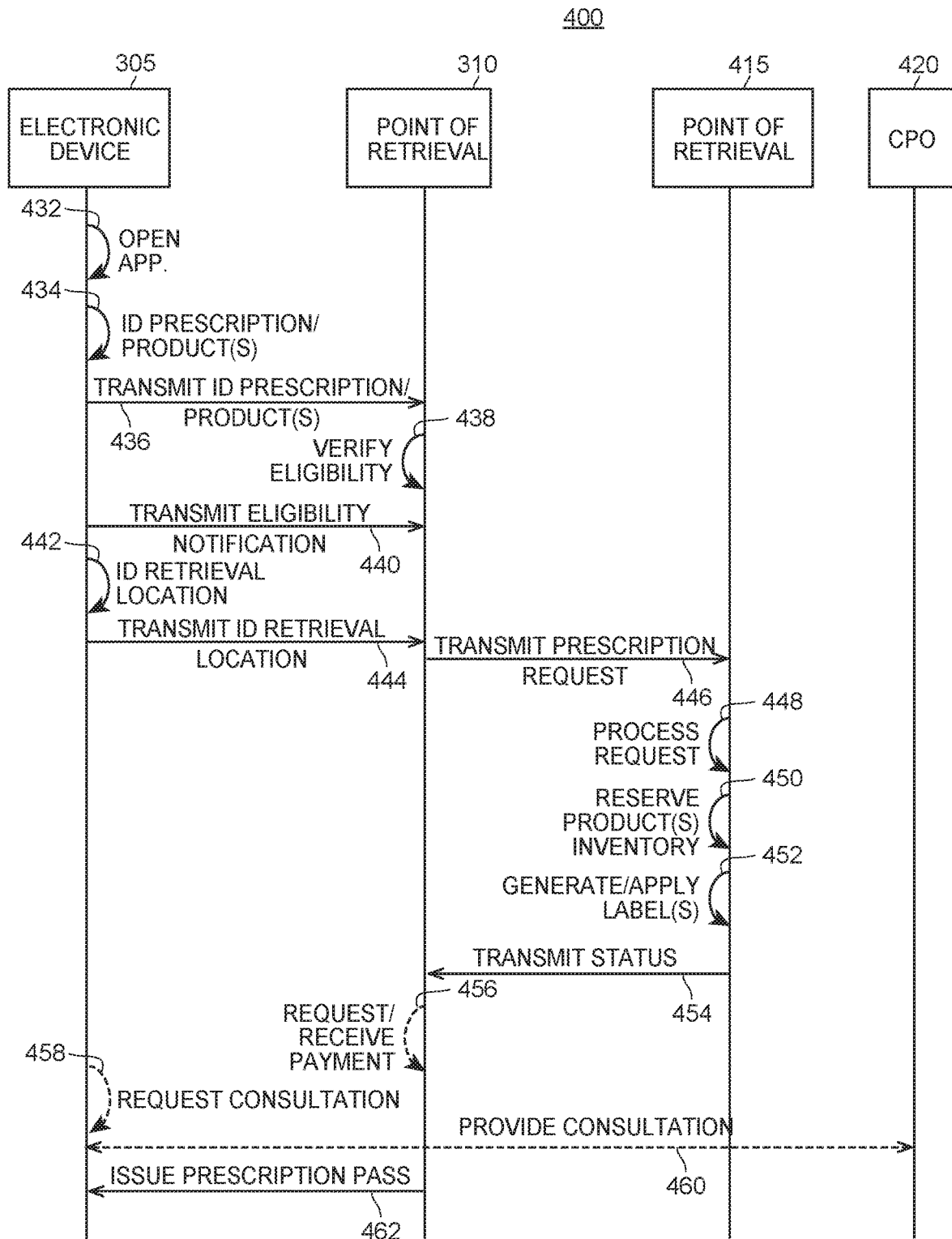
FIG. 4 depicts an example signal diagram associated with generating a unique machine-readable code redeemable to retrieve one or more prescription products, in accordance with some embodiments.

FIG. 4 depicts a signal diagram 400 associated with generating a unique machine-readable code redeemable to retrieve one or more prescription products, in accordance with some embodiments. The one or more prescription products may include products associated with a new prescription, and/or a prescription refill.

The signal diagram 400 includes an electronic device 305 (such as the electronic device 114 as discussed with respect to FIGS. 1 and 2) that may be operated by a user (e.g., a patient, or a parent, guardian, or caregiver thereof). It should be appreciated that actions attributed to the electronic device 305 in FIG. 4 may include actions performed on the electronic device 305 by a user of the electronic device 305 (e.g., a button press, data entry, etc.). The signal diagram 400 also includes a server 310 (such as the processing server 120 as discussed with respect to FIG. 1). It should be noted that, while one server is described with regard to FIG. 4, one or more servers are possible. Further, either or both of the electronic device 305 and the server 310 may be the same components as those described with regard to FIG. 3.

The signal diagram 400 additionally includes a point of retrieval system 415 (such as the point of retrieval system 140 discussed with respect to FIG. 1), and a central pharmacy operations (CPO) system 420 (such as the CPO system 160 discussed with regard to FIG. 1). It should be appreciated that additional, fewer, or alternative components, devices, and actions may be envisioned, in some embodiments. Further, one or more of the actions depicted in FIG. 4 may be omitted, in some embodiments.

The signal diagram 400 may begin when a prescription pass application is opened (432) on the electronic device 305. It should be understood that, while a prescription pass application is generally described in the signal diagram 400, other implementations (e.g., a web browser running on the electronic device 305) may be possible, in some embodiments.

Once the application is opened, a user of the electronic device 305 may identify (434) a medical prescription associated with the patient. Additionally or alternatively, the user may identify the one or more prescription products associated with the medical prescription. The user identification of the prescription/product(s) may include any suitable user interaction with the electronic device 305 (e.g., a screen tap, button press, voice command, etc.) from a provided list of medical prescriptions and/or products associated with the patient, in some embodiments. After the user identifies a medical prescription and/or product(s), the electronic device 305 may automatically transmit (436), to the server 310, an indication of the medical prescription/product(s).

After receiving the indication of the medical prescription/product(s) from the electronic device 305, the server 310 may verify (438) the eligibility of the prescription and/or product(s) for retrieval using the prescription pass technology. Verifying eligibility may include, for example, verifying that an identified prescription product is eligible to be issued and/or refilled using a prescription pass. If an identified prescription/product is not eligible, the server 310 may transmit to the electronic device 305 a notification of the lack of eligibility and/or a reason therefor. Otherwise, the server 310 may transmit (440) to the electronic device 305 a notification of the eligibility of the identified medical prescription and/or the associated prescription product(s).

Once eligibility of the medical prescription is confirmed, the user of the electronic 305 may identify (442) a location for retrieval of the one or more prescription products. Identifying a retrieval location may include, for example, identifying a venue such as a hospital or pharmacy, or more specifically, identifying a particular point of retrieval such as pharmacy counter, automated drop box, kiosk. In some embodiments, identifying a retrieval location may, even more specifically, include identifying a particular one of multiple service stations at a particular point of retrieval, as will be discussed further in this detailed description. The user of the electronic device 305 may identify the retrieval location, for example, via a suitable user interaction with the electronic device 305 (e.g., a screen tap, button press, voice command, etc.) from a provided list of nearby potential retrieval locations, in some embodiments.

After the user identifies a retrieval location, the electronic device 305 may automatically transmit (444), to the server 310, an indication of the identified retrieval location. In response to receiving the indication, the server 310 may transmit (446) a prescription product/refill retrieval request to the point of retrieval system 415 associated with the identified retrieval location (e.g., a computing device, such as a pharmacy counter computer or an automated prescription kiosk or drop box) associated with the identified point of retrieval. The request may, for example, identify the associated prescription, the associated product(s), request may additionally identify the patient, the representative of the patient (if applicable), one or more prerequisite tasks (e.g., product/inventory reservation, labeling, etc.) to be performed by the point of retrieval system 415, and/or more information regarding the medical prescription.

It should be noted that actions of the point of retrieval system 415, as described herein, may include actions performed a computing device at the point of retrieval system associated with the identified retrieval location, and/or actions performed by a person or persons (e.g., a pharmacist) at the identified retrieval location (e.g., in a brick-and-mortar environment and/or through interaction with the computing device at the point of retrieval), where appropriate.

In any case, upon receiving the request, the point of retrieval system 415 may process (448) the prescription product/refill retrieval request. Processing the request may, in some embodiments, include verifying that the requested one or more prescription products or product refills may be issued at the particular point of retrieval. If, during the processing, the point of retrieval system 415 determines that the requested products or refills cannot be issued at the particular point of retrieval for any reason (e.g., size of a product, lack of inventory, etc.), the point of retrieval system 415 may notify the server 310, which may in turn notify the user via the electronic device 305. In response, the user may identify a different retrieval location in a manner similar to that described above.

In some embodiments, after processing the request, the point of retrieval system 415 may reserve products and/or inventory (450) for the one or more prescription products to be retrieved. In some implementations, reserving a product may include a reserving a product item itself (e.g., a claim to a medication or medical device currently on or pending delivery to a pharmacy shelf). Reserving inventory may, for example, include reserving a portion of a limited physical quantity of space for a product to be retrieved (e.g., a limited storage capacity inside a prescription kiosk or drop box).

Further, in some embodiments, the point of retrieval system 415 may automatically generate one or more labels and/or apply the one or more labels (452) to the one or more prescription products. The generation and/or application of the one or more labels may be caused via a request from the server 310, for example. The one or more labels may include, for example, information identifying the one or more prescription products and/or the patient for whom the one or more prescription products will be issued.

Once request processing and any additional tasks are completed, the point of retrieval system 415 may transmit (454), to the server 310, an update of status of the prescription product/refill request. The status update may include, for example, an indication of the preparedness of the one or more products for retrieval, an anticipated time of preparedness for retrieval, a cost of the one or more prescription products, and/or an indication of one or more additional tasks (e.g., product/inventory reservation, labeling, etc.) performed with regard to the request.

At any time after a cost of the one or more prescription products is determined (e.g., upon identification of the one or more prescription products by the user, or upon processing of the prescription product/refill request by the point of retrieval system 415), the server 310 may, in some embodiments, request and/or receive payment (456) for the one or more prescription products from the user via the electronic device 305. In some possible embodiments, the user may configure the electronic device 305 (e.g., configure the application) to automatically and/or manually provide payment from the account of the user. In any case, various payment methods may be enabled, including but not limited to credit card, debit card, Apple Pay®, HSA/FSA payment, etc.

In some embodiments, the user may request (458), from the electronic device 305 to the server 310, a consultation with a remotely-located pharmacist regarding the patient's prescription and/or product(s). In response to the request, a communication session may be established and a consultation (e.g., via text messaging, video messaging, voice call, etc.) provided (460) between the user the electronic device 305 and a remotely-located pharmacist at an appropriate central pharmacy operations (CPO) system 420. While the consultation in FIG. 4 is depicted as occurring after request processing and payment, it should be appreciated that other implementations may be possible. In some embodiments, a prescription pass application may enable the user to connect with a pharmacist at the CPO system at any time (e.g., any point during flow of the signal diagram 400). Some medical prescriptions and/or prescription products may require such a consultation at some point prior to issuance of a prescription pass.

Once the point of retrieval system 415 has transmitted a status indicating preparedness or future preparedness of the one or more prescription products for retrieval, the server 310 may issue (462) a prescription pass to the user at the electronic device 305. The prescription pass may include a unique machine-readable code, such as a barcode, two-dimensional matrix barcode (e.g., QR code), alphanumeric code, sound file, or some other unique machine-readable code that a user of the electronic device 305 may scan at a point of retrieval to identify the medical prescription and/or the product(s) to retrieve. The server 310 may issue the prescription pass, for example, to the electronic device 305 for the user to view via the prescription pass application, and/or otherwise through SMS text, MMS text, email, and/or another suitable form of file transfer. Additionally or alternatively, the electronic device 305 may access the prescription pass (at the time of scanning, for example) from the server 310 via a network connection (e.g., through the prescription pass application or a website). In any case, the prescription pass may be printable, in some embodiments, allowing the user to redeem the prescription pass at a retrieval location via a printed document.

In some embodiments, the prescription pass may be transferable, allowing the user to transfer the prescription pass to another person, such as from a patient to a representative thereof (e.g., via a user interaction at the prescription pass application). In some embodiments, transferal of a prescription pass may include reissuance of the prescription pass to the other person. Additionally or alternatively, in some embodiments, a user may cancel an issued or otherwise in-progress prescription pass. Prescription pass cancellation ("reversal") and/or transferal may be enabled, for example, via communication between the electronic device 305 and the server 310 via the prescription pass application described herein, via a web browser, via an email or SMS client, and/or via other techniques.

In some embodiments, the user may, while requesting a prescription pass, configure one or more notifications associated with the prescription pass. For example, the user may configure a notification to be transmitted to the user at a time at which the one or more prescription products are prepared for retrieval by the user. User configuration of a notification may include configuration of one or more messages (e.g., a message within the prescription pass application, a push notification, an SMS message, an email, a voice call, etc.) to be transmitted form the server 310 to the electronic device 305 and/or to another device associated with the user. In some embodiments, a configured notification may include location-based notification. For example, a user may configure a notification to be transmitted to the user at a time when the user is within a specified geographic proximity to the point of retrieval system 415 while the one or more prescription products are prepared for retrieval. Location-based notifications may be enabled, for example, via opt-in location sharing between the electronic device 305 and the server 310. In some embodiments, the server 310 may automatically configure one or more notifications during issuance of the prescription pass.

Redeeming a Prescription Pass and Issuing Prescription Product(S)

Figure 5:
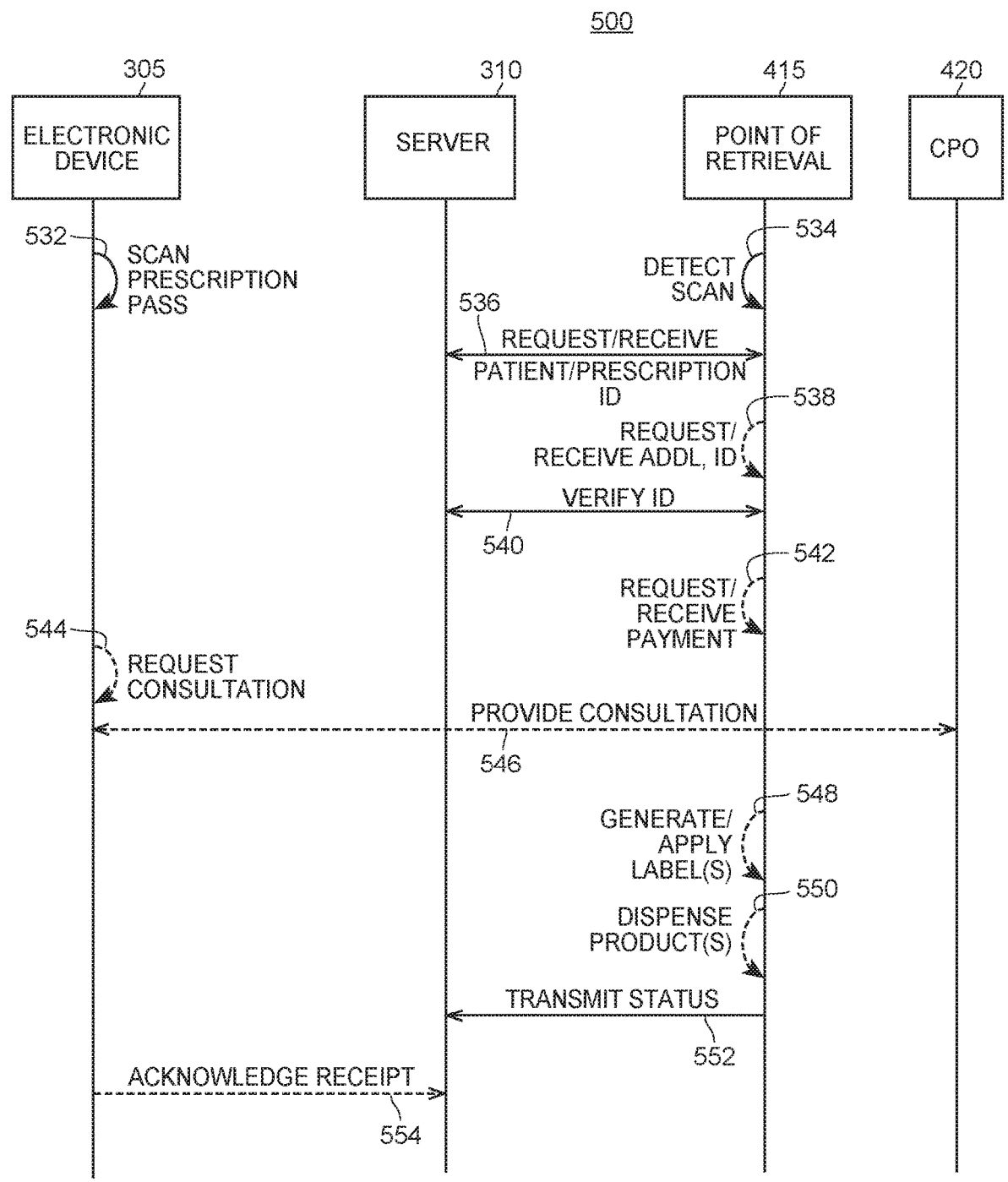
FIG. 5 depicts an example signal diagram associated with issuing one or more prescription products, in accordance with some embodiments.

FIG. 5 depicts a signal diagram 500 associated with issuing one or more prescription products, in accordance with some embodiments. The one or more prescription products may include products associated with a new prescription, and/or a prescription refill.

The signal diagram 500 includes an electronic device 305 (such as the electronic device 114 as discussed with respect to FIGS. 1 and 2) that may be operated by a user (e.g., a patient, or a parent, guardian, or caregiver thereof). It should be appreciated that actions attributed to the electronic device 305 in FIG. 5 may include actions performed on the electronic device 305 by a user of the electronic device 305 (e.g., a button press, data entry, etc.). The signal diagram 500 also includes a server 310 (such as the processing server 120 as discussed with respect to FIG. 1). While one server 310 is described herein for ease of description, it should be appreciated that one or more servers 310 may be possible.

The signal diagram 500 additionally includes a point of retrieval system 415 (such as the point of retrieval system 140 discussed with respect to FIG. 1), and a central pharmacy operations (CPO) system 420 (such as the CPO system 160 discussed with regard to FIG. 1). It should be appreciated that additional, fewer, or alternative components, devices, and actions may be envisioned, in some embodiments. Further, one or more of the actions depicted in FIG. 5 may be omitted, in some embodiments. One or more of the electronic device 305, the server 310, the point of retrieval system 415, and the CPO system 520 may be the same components as those described with regard to FIG. 3 and/or FIG. 4.

While in vicinity of the point of retrieval system 415, the user of the electronic device 305 may scan or visually present (532) the unique prescription pass previously provided to or accessed by the electronic device 305 via the server 310. Scanning or visually presenting the prescription pass at the point of retrieval system 415 may include, for example, the user of the electronic device 305 causing an interaction (e.g., a display via a user interface, a swipe, sound play, etc.) between the electronic device 305 and a scanning unit at the point of retrieval system 415. Additionally or alternatively, the user may scan a printed code, without use of the electronic device 305. In any case, the point of retrieval system 415 may detect (534) the scan (e.g., by detecting the prescription pass' unique machine-readable code via a scanning unit of a computing device at the point of retrieval).

In some embodiments, the point of retrieval system 415 may request and receive (536), from the server 310, an identification of the patient, prescription, and/or product(s) associated with the prescription based on the detected prescription pass scan. The identification may be provided based on a stored record at the server 310, associating the prescription pass' unique machine-readable code with the patient, medical prescription, and/or prescription product(s). In another possible embodiment, the point of retrieval system 415 may store the above described information at an internal memory, and retrieve, from the internal memory, the patient, prescription, and/or product(s) associated with the scanned prescription pass.

In some embodiments, additional security measures may be required at the point of retrieval system 415 before one or more prescription products can be dispensed. For example, the point of retrieval system 415 may request and receive (538) additional identification (e.g., a phone number, PIN, birthdate, etc.) from the user. The request of the information may be displayed, for example, via a point of retrieval system 415 display screen, and the information received via an interaction by the user at a point of retrieval system 415 I/O unit (e.g., a button press, touch screen interaction, audio prompt, etc.). The point of retrieval system 415 may verify (540) the additional identification via another interaction with the server 310, and/or via stored user, patient, prescription, or product data at the point of retrieval system 415.

In some embodiments (e.g., if the user has not already provided payment for the one or more prescription products to be retrieved), the point of retrieval system may request and receive (542) payment for the one or more prescription products. The point of retrieval system 415 may request and/or receive payment via one or more user interfaces (e.g., display screens), and/or one or more I/O units (e.g., a card scanner, touch screen, keypad, etc.) at the point of retrieval system 415. Additionally or alternatively, the user may provide payment via the electronic device 305 in a manner similar to that described regarding the payment action 456 in FIG. 4. In any case, various payment methods may be enabled, including but not limited to credit card, debit card, Apple Pay®, HSA/FSA payment, etc.

In some embodiments, the user may request (544), from the electronic device 305 to the server 310, a consultation with a remotely-located pharmacist regarding the patient's prescription and/or product(s). In response to the request, a communication session may be established and a consultation provided (546) between the user the electronic device 305 and a remotely-located pharmacist at an appropriate central pharmacy operations (CPO) system 420. While the consultation in FIG. 5 is depicted as occurring after prescription pass scanning and payment, it should be appreciated that other implementations may be possible. In some embodiments, a prescription pass application may enable the user to connect with a pharmacist at the CPO system at any time (e.g., any point during flow of the signal diagram 500). Some medical prescriptions and/or prescription products may require such a consultation a product may be dispensed at the point of retrieval system 415.

In some embodiments, the point of retrieval system 415 may automatically generate one or more labels and/or apply the one or more labels (458) to the one or more prescription products. The generation and/or application of the one or more labels may be caused via a request from the server 310, for example. The one or more labels may include, for example, information identifying the one or more prescription products and/or the patient for whom the one or more prescription products will be issued.

Once the prescription pass has been identified and any additional necessary actions are completed, the point of retrieval system 415 may dispense (550) the one or more prescription products. The point of retrieval system 415 may dispense the product(s), for example, automatically via one or more dispensing units (e.g., within a prescription kiosk or drop box).

Once the point of retrieval system 415 has dispensed the one or more prescription products to the user, the point of retrieval system 415 may transmit (552), to the server 310, an indication of the status of the prescription processing. The transmitted status may include, for example, an indication that the one or more prescription products have been dispensed, and/or an indication of one or more additional actions (e.g., payment) completed at the point of retrieval system 415. Meanwhile, the user, via the electronic device 315, may acknowledge receipt (354) of the one or more prescription products, in some embodiments.

"Drive-Thru" Prescription Product Retrieval

In some instances, a point of retrieval for prescription products within a venue may comprise multiple service stations. For example, a pharmacy may achieve a point of retrieval in the form of a "drive-thru" whereby passengers within vehicles may retrieve prescription products at the exterior of the venue. In some implementations, an autonomous vehicle without a passenger(s) may access a point(s) of retrieval. The drive-thru point of retrieval may comprise multiple service stations (or "lanes") whereby multiple persons may concurrently retrieve prescription products. As another example, a pharmacy counter within a hospital may comprise a plurality of stations concurrently serving individuals retrieving prescription products. Even in such configurations, however, individuals retrieving prescriptions may conventionally encounter significant wait time before a station becomes available.

While the prescription pass technology described herein offers benefits to individuals retrieving prescription products from points of retrieval comprising any number of service stations, specific implementations of the prescription pass technology may offer particular benefits to the product retrieval experience at points of retrieval comprising multiple stations, as will be described in this section. While a "drive-thru" example may generally be referred to in this section, it should be understood that the described concepts may be applied to other points of retrieval comprising two or more stations for retrieving prescription products.

Figure 6:
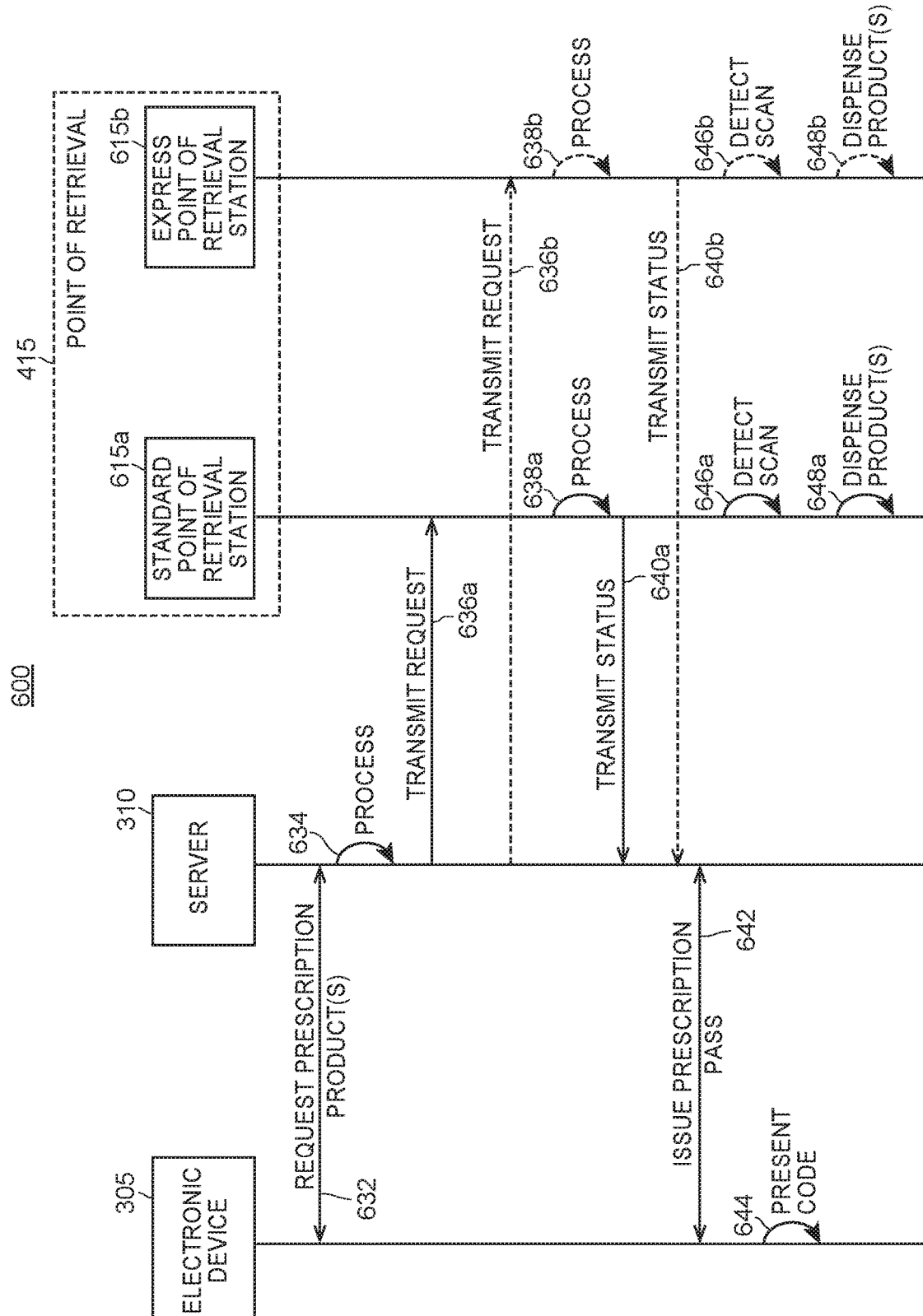
FIG. 6 depicts an example signal diagram associated with "drive-thru" retrieval of one or more prescription products, in accordance with some embodiments.

FIG. 6 depicts an example signal diagram 600 associated with drive-thru retrieval of one or more prescription products, in accordance with some embodiments. Generally, a drive-thru point of retrieval within a venue (e.g., exterior of a pharmacy), may comprise multiple stations or "lanes," including one or more "express stations" configured specifically to serve individuals retrieving prescription products using the prescription pass technology. Use of an express station may significantly quicken prescription product retrieval for prescription pass users, and further may incentivize additional users to utilize the prescription pass technology discussed throughout this detailed description. The express station may thus result in reduced service times and wait times for individuals retrieving prescription products.

The signal diagram 600 includes an electronic device 305 (such as the electronic device 114 as discussed with respect to FIGS. 1 and 2) that may be operated by a user (e.g., a patient, or a parent, guardian, or caregiver thereof). It should be appreciated that actions attributed to the electronic device 305 in FIG. 6 may include actions performed on the electronic device 305 by a user of the electronic device 305 (e.g., a button press, data entry, etc.). The signal diagram 600 also includes a server 310 (such as the processing server 120 as discussed with respect to FIG. 1). It should be noted that, while one server is described with regard to FIG. 6, one or more servers are possible. Further, either or both of the electronic device 305 and the server 310 may be the same components as those described with regard to FIG. 3.

The signal diagram 600 additionally includes a point of retrieval system 415 (which may be the point of retrieval system 140 discussed with respect to FIG. 1, for example) disposed within a venue, such as a pharmacy. The point of retrieval system 415 may be distributed among a "standard" point of retrieval station 615a and an "express" point of retrieval station 615b. While one standard station 615a and one express station 615b are described herein, it should be understood that one or more of each are possible. The stations may generally be collocated within (i.e., inside or generally around) the venue. Each station 615a-615b may comprise one or more computing devices, drop boxes, kiosks, dispensing units, etc.

It should be appreciated that additional, fewer, or alternative components, devices, and actions may be envisioned, in some embodiments. In particular, it is noted that the signal diagram 600 is generally presented to describe concepts particular to venues with multiple points of retrieval. Other elements discussed in this detailed description, even if not present in the signal diagram 600, may be included (e.g., as part of the actions depicted in FIG. 6), unless specifically indicated otherwise. Further, one or more of the actions depicted in FIG. 6 may be omitted, in some embodiments. One or more of the electronic device 305, the server 310, and the point of retrieval system 415, may be the same components as those described with regard to FIGS. 3, 4, and/or 5.

The signal diagram 600 may begin with a request (632) for retrieval of one or more prescription products (e.g., a new product or a product refill), the request initiated by the electronic device 305 (e.g., by the user of the electronic device 305). The prescription product/refill request may include one or more device and/or server actions described with regard to prescription product requests in FIGS. 4 and/or 5 (e.g., identifying a medical prescription, identifying products, verifying eligibility, etc.). In particular, the request may include identification of a desired retrieval location, such as a point of retrieval comprising multiple service stations.

Once the prescription product(s) have been requested, the server 310 may process (634) the prescription product/refill request. Processing the request may include, for example, receiving indication of one or more tasks performed by the individual associated with retrieval of the prescription (e.g., patient, caregiver, etc.), wherein the tasks may be prerequisite to retrieving the one or more prescription products. Such tasks may include, for example, payment for the one or more prescription products, acceptance of a privacy notice, completion of a consultation with a remotely-located pharmacist, processing of an insurance claim, etc. One or more of the tasks may be completed, for example, by the individual associated with retrieval of the prescription product(s) via a prescription pass application on the electronic device 305, which may be in communication with the server 310.

Completion of one or more of the above-described tasks prior to retrieval of the one or more prescription product (or, prior to issuance of a prescription pass) may determine a "completion status" of the prescription. The server 310 and/or the point of retrieval system 415, for example, may determine a completion status based upon a particular task completed, a particular task not completed, a total number or weight of tasks completed, etc. Generally, prescriptions having a completion status indicating more prerequisite tasks completed (i.e., fewer outstanding tasks) may be more likely to be enabled to use an express station at the point of retrieval, as such tasks will not need to be performed at the point of retrieval itself (which would potentially induce wait times at the point of retrieval). In some embodiments, the use of the prescription pass technology may alone be sufficient for eligibility or to utilize an express station, regardless of additional tasks that may be necessary at the point of retrieval.

After processing the prescription product/refill request, the server 310 may transmit a prescription product/refill request the point of retrieval system 415. In some embodiments, the request transmitted by the server 310 may include an indication of whether the prescription product/refill request is eligible to be fulfilled an express station 615b, based upon the completion status. Alternatively, the request may include an indication of one or more prerequisite tasks completed, from which the point of retrieval system 415 may determine whether the request is eligible to be completed via the express station 615b.

The request may, for example, identify the associated prescription, the associated product(s), the patient, the representative of the patient (if applicable), one or more prerequisite tasks (e.g., product/inventory reservation, labeling, etc.) to be performed by the point of retrieval system 415, and/or more information regarding the medical prescription.

In response to a received request from the server 310, the point of retrieval system 415 may process the request for fulfillment at the standard station 615a or the express station 615b (638a and 638b, respectively). Processing the request may, in some embodiments, include verifying that the requested one or more prescription products or product refills may be issued at the particular station. If, during the processing, the point of retrieval system 415 determines that the requested products or refills cannot be issued at the particular point of retrieval for any reason (e.g., size of a product, lack of inventory, etc.), the point of retrieval system 415 may notify the server 310, which may in turn notify the user via the electronic device 305. In response, the user may identify a different retrieval location. Additionally or alternatively, processing the request may include other actions of a point of retrieval system 415 described in this detailed description, including a product and/or inventory reservation, generation and/or application of a label, etc. In some embodiments, the above actions of the point of retrieval system 415 may be specifically performed via one or more computing devices at stations 615a and/or 615b.

Once a point of retrieval system 415 processes the request, the point of retrieval system 415 may transmit (640a-640b), to the server 310, an update of status of the prescription product/refill request. The status update may include, for example, an indication of the preparedness of the one or more products for retrieval, an anticipated time of preparedness for retrieval, a cost of the one or more prescription products, and/or an indication of one or more prerequisite tasks (e.g., product/inventory reservation, labeling, etc.) performed or yet to be performed with regard to the request.

Once the server 310 has received indication of processing of the prescription product/refill request at a point of retrieval 415, the server 310 may issue (642) a prescription pass to the individual associated with the retrieval, via the electronic device 305. The prescription pass may include a unique machine-readable code, such as a barcode, two-dimensional matrix barcode (e.g., QR code), alphanumeric code, sound file, or some other unique machine-readable code that a user of the electronic device 305 may scan at a point of retrieval to identify the medical prescription and/or the product(s) to retrieve. The server 310 may issue the prescription pass, for example, to the electronic device 305 for the user to view via the prescription pass application, and/or otherwise through SMS text, MMS text, email, and/or another suitable form of file transfer. Additionally or alternatively, the electronic device 305 may access the prescription pass (at the time of scanning, for example) from the server 310 via a network connection (e.g., through the prescription pass application or a website).

In some embodiments, the prescription pass may specifically indicate whether or not the prescription product/refill request is presently eligible for retrieval at an express station 615b, or whether retrieval must occur at the standard station 615a. In some embodiments, even if the request is not eligible for express eligible at the time of issuance of the prescription pass, the individual may, in some embodiments, cause the request to become eligible by performing one or more prerequisite tasks in advance of the retrieval. Completion of such tasks may result in issuance of an updated prescription pass. Alternatively, in other embodiments, the prescription pass may not make any particular indication of express station eligibility or lack thereof, and such indication may be provided at the point of retrieval itself (e.g., at a check-in station at the point of retrieval but prior to the standard or express station).

At the time of retrieval, the individual associated with the retrieval may scan or otherwise present (644) the unique machine-readable code via the electronic device 305. Scanning or visually presenting the prescription pass at a point of retrieval system may include, for example, the user of the electronic device 305 causing an interaction (e.g., a display via a user interface, a swipe, sound play, etc.) between the electronic device 305 and a scanning unit at the point of retrieval system 415 (e.g., more specifically, the standard point of retrieval station 615a or the express point of retrieval station 615b). Additionally or alternatively, scanning the electronic device may include scanning a printed document, without use of the electronic device 305. In some embodiments, presenting the code may include first presenting the code at a check-in station prior to the standard/express stations 615a-615b, to identify from which station the retrieval is to be achieved.

The standard station 615a or the express station 615b may detect (646a and 646b, respectively) the scan (e.g., by detecting the prescription pass' unique machine-readable code via a scanning unit of a computing device at the station, or alternatively, by receiving an indication from another part of the point of retrieval system 415). Detecting the scan may include identifying the patient, the individual associated with the retrieval, the medical prescription, and/or the one or more prescription products, based upon the unique machine-readable code. Once the prescription pass has been identified, the station 615a or 615b may dispense (648a and 648b, respectively) the one or more prescription products. The point of retrieval station 615a or 615b may dispense the product(s), for example, automatically via one or more dispensing units (e.g., within a prescription kiosk or drop box). Dispensing the one or more prescription products may first include facilitation of one or more outstanding tasks (consultation, payment, identification, etc.) that may be prerequisite to retrieving the one or more prescription products.

EXAMPLE METHODS

Figure 7:
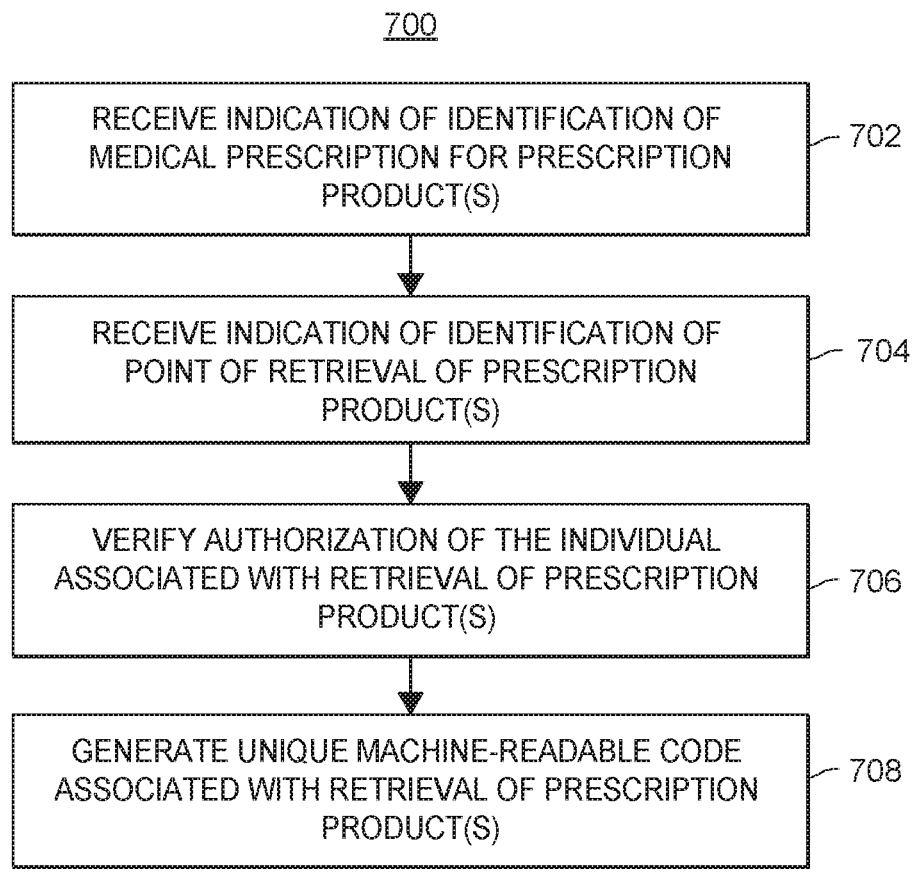
FIG. 7 depicts an example computer-implemented method for generating a unique machine-readable code redeemable to retrieve one or more prescription products.

FIG. 7 depicts an example computer-implemented method 700 for generating a unique machine-readable code redeemable to retrieve one or more prescription products. Generally, the unique machine-readable code may be generated and/or issued to an electronic computing device of an individual as a "prescription pass." The method 700 may be performed, for example, via the system 100 described with regard to FIGS. 1 and 2.

The method 700 may include receiving, via one or more processors, a first indication of identification of a medical prescription for one or more prescription products (e.g., a medication or medical device), the first indication originating from a computing device (e.g., a smartphone, laptop computer, desktop computer, tablet, etc.) of an individual associated with a retrieval of the one or more prescription products (702).

The individual associated with the retrieval may be, for example, an individual associated with the medical prescription itself (e.g., a patient to whom the prescription is prescribed). Alternatively, the individual may be another individual who is a representative of the patient (e.g., a parent, guardian, caregiver, etc.). The first indication may be received, for example, via one or more processors of one or more backend servers, and from an electronic device of a user (e.g., a patient, parent, guardian, or caregiver) seeking retrieval of one or more prescription products (i.e., products or product refills) associated with the identified medical prescription. The first indication may include, for example, an interaction by the user from a list of available or eligible prescriptions listed in a prescription pass mobile or web application.

The method 700 may also include receiving, via one or more processors, a second indication of identification of a point of retrieval of the one or more prescription products, the second indication originating from the computing device of the individual associated with the retrieval of the one or more prescription products (704). The identified point of retrieval may include, for example, a particular pharmacy counter, a prescription kiosk or drop box, and/or another appropriate point of retrieval. In any case, the point of retrieval may be identified, for example, from a list of available and/or nearby retrieval locations presented in the prescription pass application.

The method 700 may also include verifying, via the one or more processors, an authorization of the individual associated with the retrieval of the one or more prescription products to retrieve the one or more prescription products at the point of retrieval (706). The verification may include, for instance, verifying that the medical prescription and/or product(s) are eligible to be retrieved using the prescription pass technology. Additionally or alternatively, the verification may include verifying that a representative of the patient (e.g., a parent, guardian, or caregiver) is authorized to retrieve the particular one or more prescription products on behalf of the patient.

The method 700 may further include generating, via the one or more processors, a unique machine-readable code associated with retrieval of the one or more prescription products, wherein the unique machine-readable code is associated with the medical prescription (708). The unique machine-readable code may include, for example, a barcode, two-dimensional matrix barcode (e.g., QR code), audio file, alphanumeric code, and/or another code. In any case, in some embodiments, the generated machine-readable code may be associated specifically with the identified point of retrieval. In other words, the machine-readable code may, in some embodiments, be redeemable only at the identified point of retrieval, whereas, in other embodiments, other points of retrieval may be possible. The method 600 may further include transmitting the unique machine-readable code to the computing device associated with the retrieval of the one or more prescription products.

In some embodiments, the method 700 may further include causing, via the one or more processors, one or more product reservations and/or spatial reservations at the point of retrieval. A spatial reservation may include, for example, a reservation of a portion of a limited physical quantity of space for a product to be retrieved (e.g., a limited storage capacity inside a prescription kiosk or drop box). A product reservation may include, for example, reservation of a product item itself (e.g., a claim to a medication or medical device currently on or pending delivery to a pharmacy shelf, such that the product will not be out of stock at the time of retrieval). In any case, a reservation may be caused, for example, via communication from a backend server to a computer system and/or individual at the identified point of retrieval.

In some embodiments, the method 700 may further include causing, via the one or more processors, one or more labels to be applied to one or more containers associated with the one or more prescription products, wherein the one or more labels identify the one or more prescription products and a patient associated with the medical prescription.

In some embodiments, the method 700 may further include processing a payment for the one or more prescription products. Processing a payment may, for example, include receiving, via the one or more processors, an indication of payment for the one or more prescription products by the individual. An indication of payment may be received, for example, at a backend server after payment from the computing device of the individual. In some embodiments, payment may be required prior to issuance of a unique machine-readable code.

In some embodiments, the method 700 may further include (i) receiving, via the one or more processors, a request to communicate with a remote pharmacist, the request initiated by the individual, and/or (ii) causing, via the one or more processors, a communication session to be initiated between the computing device of the individual and a computing device of the remote pharmacist. The communication session may, for example, enable the individual to communicate information to and/or receive instruction from the remotely-located pharmacist. In some embodiments, a particular prescription and/or product may require such a communication session to occur prior to issuance of a unique machine-readable code. In these embodiments, the unique machine-readable code may be generated in response to an authorization granted by the remote pharmacist after the communication session.

In some embodiments, the method 700 may further include configuration of one or more notifications associated with the prescription pass. Notification configuration may include, for example, configuration of a notification (e.g., push notification, voice call, SMS message, email, or another message within a prescription pass application) to be transmitted to one or more electronic devices at a time at which the one or more prescription products are prepared for retrieval by the individual. A notification may be configured manually by the individual and/or automatically via the one or more processors, in some embodiments.

The method 700 may include additional, fewer, or alternate actions, including those described in this detailed description.

Figure 8:
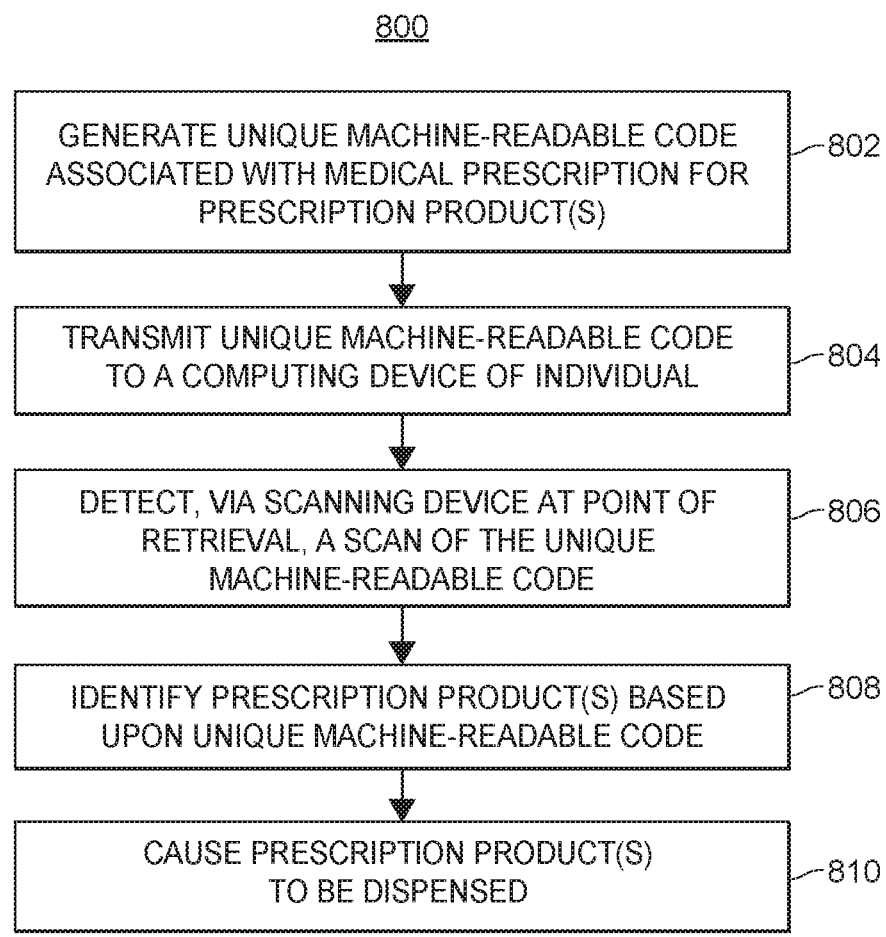
FIG. 8 depicts an example computer-implemented method for issuing one or more prescription products.

FIG. 8 depicts an example computer-implemented method 800 for issuing one or more prescription products. Generally, one or more prescription products may be issued in response to a scan of a unique machine-readable code included in a "prescription pass" provided to an individual. The method 800 may be performed, for example, via the system 100 described with regard to FIGS. 1 and 2.

The method 800 may include generating, via one or more processors, a unique machine-readable code associated with a medical prescription for one or more prescription products (802). The unique machine-readable code may include, for example, a barcode, two-dimensional matrix barcode (e.g., QR code), audio file, alphanumeric code, and/or another code. In any case, in some embodiments, the generated machine-readable code may be associated specifically with the identified point of retrieval. In other words, the machine-readable code may, in some embodiments, be redeemable only at the identified point of retrieval, whereas, in other embodiments, other points of retrieval may be possible.

The method 800 may also include transmitting (e.g., via text message, email, delivery to a prescription pass application, etc.) the unique machine-readable code to a computing device of an individual associated with a retrieval of the one or more prescription products (804). The individual associated with the retrieval may be, for example, an individual associated with the medical prescription itself (e.g., a patient to whom the prescription is prescribed). Alternatively, the individual may be another individual who is a representative of the patient (e.g., a parent, guardian, caregiver, etc.). The computing device of the individual may include, for example, a smartphone, desktop computer, laptop computer, tablet, etc.

The method 800 may also include detecting, via a scanning device at a point of retrieval of the one or more prescription products, a scan of the unique machine-readable code, the scan initiated by the individual at the point of retrieval (806). The scanning device may be, or be included within, a computing system at the point of retrieval. "Scanning" the unique machine-readable code may include, for example, swiping the computing device of the individual associated with the retrieval, presenting the code via a user interface, and/or some other visual presentation of the unique machine-readable code.

The method 800 may also include identifying, via the one or more processors, the one or more prescription products associated with the medical prescription, based upon the detected scan of the unique machine-readable code (808). Identifying the one or more prescription products may include associating the scanned code with the medical prescription based on data stored at a backend server and/or at a computing system at the point of retrieval.

The method 800 may also include causing, via the one or more processors, a dispensing of the one or more prescription products at the point of retrieval (810). Causing the dispensing may include transmission, from a backend server to a computing system and/or individual at the point of retrieval, of an indication to dispense the one or more products. Dispensing may be executed, for example, via an automatic dispensing unit of a point of retrieval system.

In some embodiments, the method 800 may further include (i) receiving, via the scanning device or via the one or more processors, at least one additional identifier (e.g., identity verification in the form of a phone number, PIN, etc.) associated with the individual, and/or (ii) verifying, via the one or more processors, based on the at least one additional identifier, an identity of the individual. In some embodiments, such an additional layer of identification may be required prior to dispensing of one or more prescription products, effectively verifying that the person at the point of retrieval is in fact the individual to whom the prescription pass was issued.

In some embodiments, the method 800 may further include causing, via the one or more processors, one or more labels to be applied to one or more containers associated with the one or more prescription products, wherein the one or more labels identify the one or more prescription products and a patient associated with the medical prescription. In some embodiments, the method 800 may further include (i) causing, via the one or more processors, a transmission one or more images of the one or more labels to a remote pharmacist, and/or (ii) receiving, via the one or more processors, an indication of verified accuracy of the one or more labels (e.g., accuracy of the information included therein), the indication granted by the remote pharmacist. In some aspects, a verification of accuracy by a pharmacist may be required before dispensing of the one or more prescription products.

In some embodiments, the method 800 may further include receiving, via the one or more processors, an acknowledgement of receipt of the one or more prescription products by the individual. The acknowledgement of receipt may be received, for example, at a backend server, and transmitted from a computing device of the individual.

In some embodiments, the method 800 may further include processing, via the one or more processors, a payment for the one or more prescription products. Processing a payment may, for example, include receiving, via the one or more processors, an indication of payment for the one or more prescription products by the individual. An indication of payment may be received, for example, at a backend server after payment from the computing device of the individual. In some embodiments, payment may be required prior to dispensing of the one or more prescription products.

In some embodiments, the method 800 may further include receiving, via the one or more processors, an indication of an acceptance of a privacy notice (e.g., HIPAA) by the individual. In some aspects, an indication of acceptance of a privacy notice may be required prior to issuance of the one or more prescription products.

The method 800 may include additional, fewer, or alternate actions, including those described in this detailed description.

Figure 9:
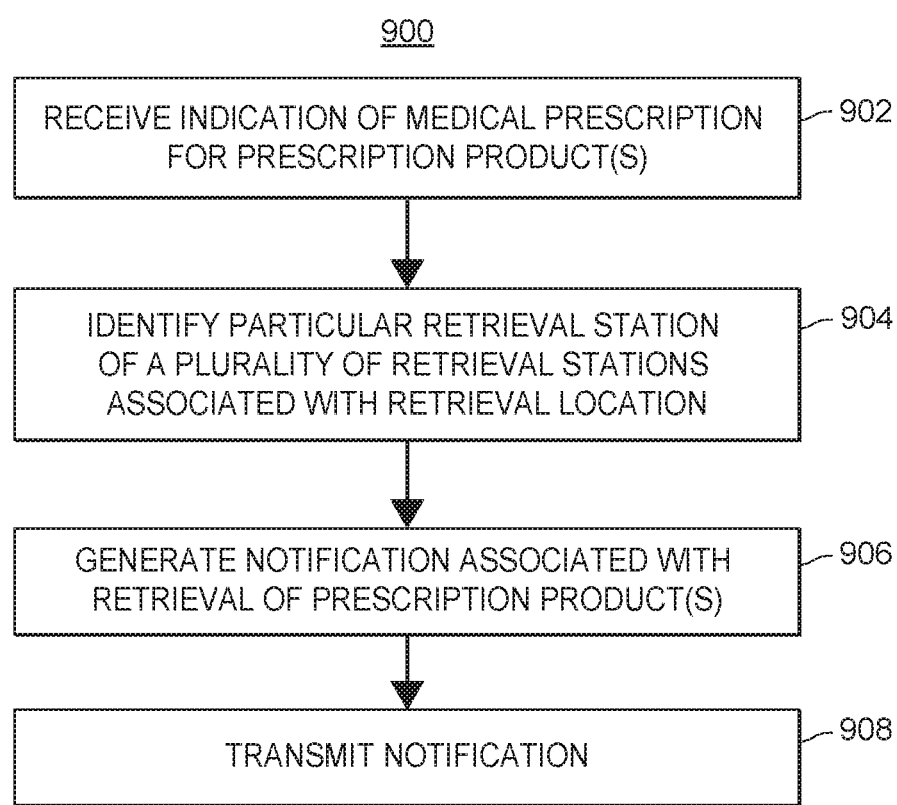
FIG. 9 depicts another example computer-implemented method for generating a unique machine readable code redeemable to retrieve one or more prescription products.

FIG. 9 depicts another example computer-implemented method 900 for generating a unique machine readable code redeemable to retrieve one or more prescription products. Generally, one or more prescription products may be issued at a particular one or multiple stations at a retrieval location (e.g., a particular point of retrieval), based upon usage of the prescription pass technology described herein and/or completion of additional prerequisite tasks prior to arriving at the retrieval location. The method 900 may be performed, for example, via the system 100 described with regard to FIGS. 1 and 2.

The method 900 may include receiving, via one or more processors, an indication of a medical prescription for one or more prescription products, wherein the indication originates from a computing device of an individual intending to retrieve the one or more prescription products, and wherein the indication identifies a retrieval location (e.g., a venue, or more specifically, a point of retrieval) for the one or more prescription products (902).

The individual intending to retrieve the one or more prescription products may be, for example, an individual associated with the medical prescription itself (e.g., a patient to whom the prescription is prescribed). Alternatively, the individual may be another individual who is a representative of the patient (e.g., a parent, guardian, caregiver, etc.). The indication may be received, for example, via one or more processors of one or more backend servers, and from an electronic device of a user (e.g., a patient, parent, guardian, or caregiver) seeking retrieval of one or more prescription products (i.e., products or product refills) associated with the medical prescription. The indication may include, for example, an interaction by the user from a list of available or eligible prescriptions listed in a prescription pass mobile or web application.

The retrieval location may include, for example, a particular pharmacy counter, a prescription kiosk or drop box, and/or another appropriate retrieval location. In any case, the retrieval location may be identified, for example, from a list of available and/or nearby retrieval locations presented in the prescription pass application. In some embodiments, the identified retrieval location may include an identification of a desired station at the retrieval location (e.g., desire to use an express station).

The method 900 may also include identifying, via the one or more processors and based upon a completion status associated with the medical prescription, a particular retrieval station of a plurality of retrieval stations associated with the retrieval location (904). A completion status may be determined, for example, based upon utilization of the prescription pass technology described herein (e.g., specifically a prescription pass mobile application), and/or based upon completion or lack of completion of one or more tasks (e.g., payment, acceptance of privacy notice, remote pharmacist consultation, etc.) prerequisite to retrieving the one or more prescription products. Prescriptions associated with a greater completion status (e.g., use of a prescription pass application, completion of more tasks, etc.) may be enabled to utilize an express station at the retrieval location instead of a standard station, thereby potentially reducing wait times for the individual at the retrieval location. In some embodiments, the completion status and/or the particular station may be determined in response to receiving the indication of the medical prescription. In at least some embodiments, however, the completion status and/or retrieval station may be determined or re-determined in response to the individual arriving at the retrieval location (e.g., at a check-in station at a point of retrieval but prior to the standard and express retrieval stations).

The method 900 may also include generating, via the one or more processors, a notification associated with retrieval of the one or more prescription products, the notification (i) comprising a unique machine-readable code, and (ii) identifying the particular retrieval station (906). The unique machine-readable code may include, for example, a barcode, two-dimensional matrix barcode (e.g., QR code), audio file, alphanumeric code, and/or another code.

The method 900 may also include transmitting (e.g., via text message, email, delivery to a prescription pass application, etc.), to the computing device via the one or more processors, the notification (908).

In some embodiments, the method 900 may further include (i) detecting, via a scanning device located at the particular retrieval station, a scan of the unique machine-readable code; (ii) identifying, via the one or more processors, the one or more prescription products associated with the medical prescription, based upon the detected scan of the unique machine-readable code; and/or (iii) causing, via the one or more processors, the one or more prescription products to be dispensed at the particular retrieval station.

In some embodiments, the method 900 may further include causing, via the one or more processors, one or more product reservations and/or spatial reservations at the retrieval location. Causing a spatial reservation may include, for example, causing a physical quantity of space to be reserved in an inventory associated with the retrieval location (e.g., a limited storage capacity inside a prescription kiosk or drop box). Causing a product reservation may include, for example, causing the one or more prescription products themselves to be reserved in an inventory associated with the retrieval location. In any case, a reservation may be caused, for example, via communication from a backend server to a computer system and/or individual at the retrieval location.

In some embodiments, the method 900 may further include causing, via the one or more processors, one or more labels to be applied to one or more containers associated with the one or more prescription products, wherein the one or more labels identify the one or more prescription products and a patient associated with the medical prescription.

In some embodiments, the method 900 may further include processing a payment for the one or more prescription products. Processing a payment may, for example, include receiving, via the one or more processors, an indication of payment for the one or more prescription products by the individual. An indication of payment may be received, for example, at a backend server after payment from the computing device of the individual. In some embodiments, payment may be required prior to issuance of a unique machine-readable code.

In some embodiments, the method 700 may further include (i) receiving, via the one or more processors, a request to communicate with a remote pharmacist, the request initiated by the individual, and/or (ii) causing, via the one or more processors, a communication session to be initiated between the computing device of the individual and a computing device of the remote pharmacist. The communication session may, for example, enable the individual to communicate information to and/or receive instruction from the remotely-located pharmacist. In some embodiments, a particular prescription and/or product may require such a communication session to occur prior to issuance of a unique machine-readable code. In these embodiments, the unique machine-readable code may be generated in response to an authorization granted by the remote pharmacist after the communication session.

In some embodiments, the method 900 may further include detecting, via the one or more processors, execution of one or more of the prerequisite tasks (e.g., payment, acceptance of privacy notice, additional identification, etc.) at the retrieval location (e.g., at the particular station), as described further in this detailed description.

The method 900 may include additional, fewer, or alternate actions, including those described in this detailed description.

ADDITIONAL CONSIDERATIONS

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed:

1. A computer implemented method for identifying one or more products according to a unique machine-readable code, the method comprising:
generating, via one or more processors, a unique machine-readable code associated with one or more prescription products to be provided to an individual at a point of retrieval;
upon generation of the unique machine-readable code, providing, via the one or more processors and via an application executing at a mobile computing device associated with the individual, (i) the unique machine-readable code, (ii) an anticipated time of preparedness of the one or more prescription products for retrieval at the point of retrieval, and (iii) an indication of one or more prerequisite tasks associated with the one or more prescription products, the one or more prerequisite tasks comprising a payment for the one or more prescription products, the one or more prerequisite tasks requiring completion by the individual prior to the retrieval at the point of retrieval;
subsequent to providing the unique machine-readable code and the indication of the one or more prerequisite tasks, receiving, via the one or more processors, payment information associated with the one or more prescription products from the mobile computing device;
subsequent to the receiving of the payment information, detecting, via a scanning device of a computing system physically located at the point of retrieval, the scan of the unique machine-readable code;
identifying, via the computing system at the point of retrieval, based upon the detected scan of the unique machine-readable code, the one or more prescription products to be provided at the point of retrieval;
determining, via the computing system at the point of retrieval, that the one or more indicated prerequisite tasks associated with the one or more prescription products have been completed, wherein determining that the one or more prerequisite tasks have been completed comprises determining that the payment information was received from the mobile computing device subsequent to the providing of the unique machine-readable code; and
responsive to determining that the one or more indicated prerequisite tasks have been completed, facilitating, via the computing system at the point of retrieval, a dispensing of the one or more prescription products at the point of retrieval.

2. The computer-implemented method of claim 1, wherein the unique machine-readable code comprises a two-dimensional matrix barcode.

3. The computer-implemented method of claim 2, wherein the unique machine-readable code further comprises an alphanumeric code.

4. The computer-implemented method of claim 1, wherein the scan is detected via a scanning of the mobile computing device.

5. The computer-implemented method of claim 1, wherein facilitating the dispensing includes causing, via the one or more processors, the one or more prescription products to be dispensed subsequent to the receiving of the payment information.

6. The computer-implemented method of claim 1, wherein receiving the payment information comprises receiving at least a portion of the payment information via a mobile computing device associated with the individual.

7. A computing system comprising:
one or more processors; and
one or more memories storing non-transitory computer-executable instructions that, when executed by the one or more processors, cause the computing system to:
generate, via the one or more processors, a unique machine-readable code associated with one or more prescription products to be provided to an individual at a point of retrieval;
upon generation of the unique machine-readable code, provide, via the one or more processors and via an application executing at a mobile computing device associated with the individual, (i) the unique machine-readable code, (ii) an anticipated time of preparedness of the one or more prescription products for retrieval at the point of retrieval, and (iii) an indication of one or more prerequisite tasks associated with the one or more prescription products, the one or more prerequisite tasks comprising a payment for the one or more prescription products, the one or more prerequisite tasks requiring completion by the individual prior to the retrieval at the point of retrieval;
subsequent to providing the unique machine-readable code and the indication of the one or more prerequisite tasks, receive, via the one or more processors, payment information associated with the one or more prescription products from the mobile computing device;
subsequent to the receiving of the payment information, detect, via a scanning device of a computing subsystem of the computing system physically located at the point of retrieval of the one or more prescription products, the scan of the unique machine-readable code;
identify, via the computing subsystem at the point of retrieval, based upon the detected scan of the unique machine-readable code, the one or more prescription products to be provided at the point of retrieval;
determine, via the computing subsystem at the point of retrieval, that the one or more indicated prerequisite tasks associated with the one or more prescription products have been completed, wherein determining that the one or more prerequisite tasks have been completed comprises determining, that the payment information was received from the mobile computing device subsequent to the providing of the unique machine-readable code; and
responsive to determining that the one or more indicated prerequisite tasks have been completed, facilitate a dispensing of the one or more prescription products via the computing subsystem at the point of retrieval.

8. The computing system of claim 7, wherein the unique machine-readable code comprises a two-dimensional matrix barcode.

9. The computing system of claim 8, wherein the unique machine-readable code further comprises an alphanumeric code.

10. The computing system of claim 7, wherein the individual is a patient having a medical prescription corresponding to at least one of the one or more prescription products.

11. The computing system of claim 7, wherein the computing system is configured to receive at least a portion of the payment information via a mobile computing device associated with the individual.

12. The computing system of claim 7, wherein the computing subsystem is configured to detect the scan via a scanning of the mobile computing device.

13. One or more computer-readable media storing non-transitory computer-executable instructions that, when executed via a computing system computing system to:
- generate, via one or more processors, a unique machine-readable code associated with one or more prescription products to be provided to an individual at a point of retrieval;
- upon generation of the unique machine-readable code, provide, via the one or more processors and via an application executing at a mobile computing device associated with the individual, (i) the unique machine-readable code, (ii) an anticipated time of preparedness of the one or more prescription products for retrieval at the point of retrieval, and (iii) an indication of one or more prerequisite tasks associated with the one or more prescription products, the one or more prerequisite tasks comprising a payment for the one or more prescription products, the one or more prerequisite tasks requiring completion by the individual prior to the retrieval at the point of retrieval;
- subsequent to providing the unique machine-readable code and the indication of the one or more prerequisite tasks, receive, via the one or more processors, payment information associated with the one or more prescription products from the mobile computing device;
- subsequent to the receiving of the payment information, detect, via a scanning device of a computing subsystem of the computing system physically located at the point of retrieval of the one or more prescription products, the scan of the unique machine-readable code;
- identify, via the computing subsystem at the point of retrieval, based upon the detected scan of the unique machine-readable code, the one or more prescription products to be provided at the point of retrieval;
- determine, via the computing subsystem at the point of retrieval, that the one or more indicated prerequisite tasks associated with the one or more prescription products have been completed, wherein determining that the one or more prerequisite tasks have been completed comprises determining that the payment information was received from the mobile computing device subsequent to the providing of the unique machine-readable code; and
- responsive to determining that the one or more indicated prerequisite tasks have been completed, facilitate a dispensing of the one or more prescription products via the computing subsystem at the point of retrieval.

14. The one or more computer-readable media of claim 13, wherein the unique machine-readable code comprises a two-dimensional matrix barcode.

* * * * *